United States Patent [19]

Quinlan

[11] 4,354,945

[45] Oct. 19, 1982

[54] CLARIFICATION PROCESS WITH THIAZINE QUATERNARY AMMONIUM SALTS OF POLYEPIHALOHYDRIN

[75] Inventor: Patrick M. Quinlan, Webster Groves, Mo.

[73] Assignee: Petrolite Corporation, St. Louis, Mo.

[21] Appl. No.: 271,894

[22] Filed: Jun. 9, 1981

Related U.S. Application Data

[62] Division of Ser. No. 32,036, Apr. 23, 1979, Pat. No. 4,316,007.

[51] Int. Cl.³ .................................................. C02F 1/56
[52] U.S. Cl. ........................................ 210/736; 209/5; 210/907
[58] Field of Search .................... 209/5; 210/725, 727, 210/728, 732, 735, 736, 907; 528/405

[56] References Cited

U.S. PATENT DOCUMENTS

| | | | |
|---|---|---|---|
| 3,251,852 | 5/1966 | De Groote et al. | 528/405 |
| 3,828,036 | 8/1974 | Quinlan | 544/58.1 |
| 3,998,796 | 12/1976 | Steinhardt | 210/735 |
| 4,113,709 | 9/1978 | Quinlan | 424/78 |

OTHER PUBLICATIONS

Schacht et al., Journal of Polymer Science, 16, 2343-2351, (1978).

Primary Examiner—Peter A. Hruskoci
Attorney, Agent, or Firm—Sidney B. Ring; Hyman F. Glass

[57] ABSTRACT

This invention relates to thiazine quaternary ammonium salts of polyepihalohydrin and the preparation and uses thereof. The compositions are ideally expressed by the polymer unit

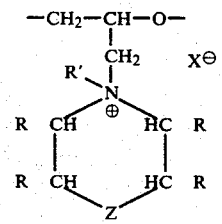

where Z is S, SO, or $SO_2$,
R is hydrogen or a hydrocarbon group,
R' is a hydrocarbon group
and X is halogen.

7 Claims, No Drawings

CLARIFICATION PROCESS WITH THIAZINE QUATERNARY AMMONIUM SALTS OF POLYEPIHALOHYDRIN

This is a division of application Ser. No. 32,036, filed Apr. 23, 1979, now U.S. Pat. No. 4,316,007.

This invention relates to thiazine quaternary ammonium salts of polyepihalohydrin, their preparation and uses.

The compositions may be ideally expressed by the polymeric unit

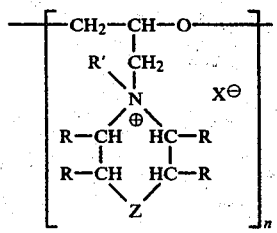

where Z is S, SO, $SO_2$, the R's are hydrogen or a substituted group such as a hydrocarbon group, i.e., alkyl, etc.; and R' is a hydrocarbon group such as alkyl, or a substituted alkyl, alkenyl, alkinyl, aryl, aralkyl, etc., n may be from about 3 to 1000, such as from 5 to 100 but preferably from 5 to 50. X is halogen, for example Cl, Br, I, F.

When divinyl sulfone is treated with a primary amine, derivatives of 1,4-thiazine-1,1-dioxide result. As references I include U.S. Pat. Nos. 3,828,036, Aug. 6, 1974 Quinlan and 4,113,709, Sept. 12, 1978 Quinlan. This reaction may be illustrated by the following general equation:

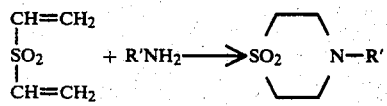

Alkyl includes methyl, ethyl, propyl, butyl, amyl, hexyl, heptyl, octyl, nonyl, decyl, undecyl, tridecyl, eicosyl, docosyl, etc. having 1–50 or more carbons, such as 1–30, but preferably 1–18 carbons.

The term "alkyl" also includes isomers of the straight chain group wherein branching occurs along the chain, for example

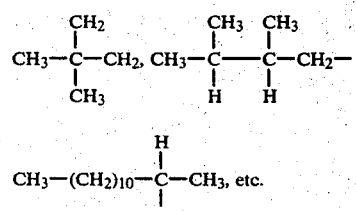

Alkenyl and alkinyl include unsaturated analogues of alkyl groups containing one or more

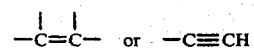

groups, for example decenyl, dodecenyl, tridecenyl, tetradecyl, pentadecenyl, hexadecyl, heptadecenyl, octadecenyl, etc., dienes for example octadienyl, etc. trienes, for example octatrienyl, etc., alkinyl, for example, butinyl, etc.

Cycloalkyl includes

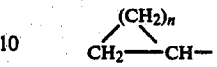

for example cyclopentyl, cyclohexyl, cycloheptyl, cyclooctyl, etc.; substituted derivatives thereof, for example alkyl cyclohexyl, dialkyl cyclohexyl, etc.

Aryl includes phenyl, substituted phenyl, alkyl phenyl, polyalkylphenyl, chlorophenyl, alkoxyphenyl, etc., naphthyl, alkyl naphthyl, etc.; benzyl, substituted benzyl, etc. groups.

Examples of divinyl sulfone compounds are:

$$CH_2=CH-S-CH=CH_2$$

$$CH_2=CH-SO-CH=CH_2$$

$$CH_2=CH-SO_2-CH=CH_2$$

Polyepichlorohydrin is prepared by conventional means for example as described in U.S. Pat. Nos. 3,058,921 and 3,251,852.

Polyepiiodohydrin is prepared by a method described by E. Schacht, et al.; *Journal of Polymer Science*, 16, 2343 (1978).

The thiazine quaternary ammonium salts of this invention may be prepared by the following general reaction.

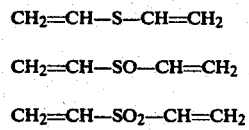

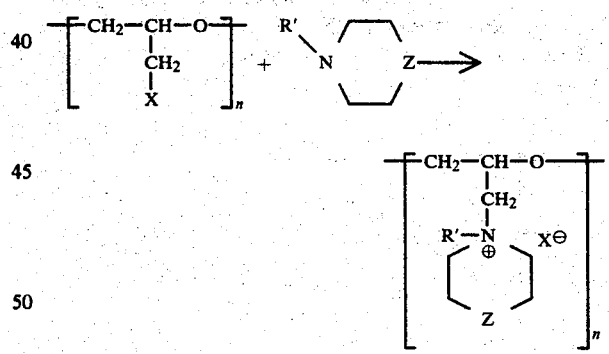

While the thiazine quaternary ammonium salts of this invention may be prepared by refluxing the polyepihalohydrin and the thiazine together in a suitable solvent or solvent mixture at atmospheric pressure, it is preferred to heat the reactants together at above atmospheric pressure in a suitable solvent or solvent mixture. This method not only lessens the reaction time but increases the yield of the desired product. Thus a reaction temperature of about 135° to about 160° C. for a period of 3 to about 24 hours in a closed reactor is preferred.

The following examples are presented for purposes of illustrating the reaction between polyepihalohydrins and various alkyl 1,4-thiazines -1,1-dioxides and are considered non-limiting.

EXAMPLE 1

Polyepichlorohydrin, M.W. 1300 (92 g; 1 eqv.) was heated at 138°-140° C. with

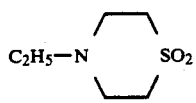

(163 g; 1 eqv) in 255 ml. of water in a closed reactor. After heating for 8 hours the ionic chloride was found to be 6.8% (Theoretical was 6.96%). The product had the following structure.

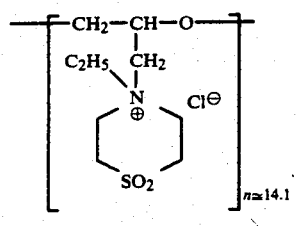

EXAMPLE 2

Polyepichlorohydrin of M.W. 1300 (92 g; 1 eqv.) was heated at 150°-160° C. with

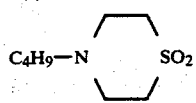

(191 g; 1 eqv.) in 287 ml. of water in a closed reactor. After 12 hours the ionic chloride was found to be 6.2% (Theoretical was 6.3%). The structure of the product was

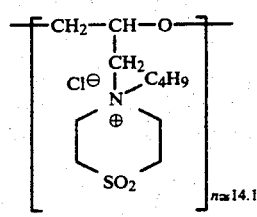

EXAMPLE 3

Polyepichlorohydrin of M.W. 1300 (92 g; 1 eqv.) was heated at 150°-160° C. with

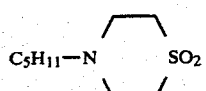

(205 g; 1 eqv.) and 297 ml. of water in a closed reactor for 18 hrs. At this time the ionic chloride content was found to be 5.8% (Theoretical was 6.0%). The structure of the product was

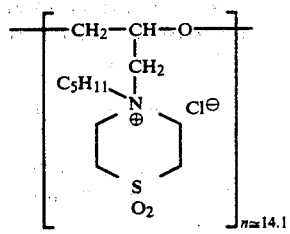

EXAMPLE 4

Polyepichlorohydrin of M.W. 1300 (92 g; 1 eqv.) was heated in a closed pressure reactor with

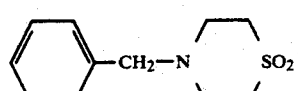

(239 g; 1 eqv.) and a 1:1 water, isopropanol mixture (331 g) at 145°-160° C. for 20 hours. At this time the ionic chloride content was found to be 5.0% (Theoretical was 5.4%). The structure of the product was

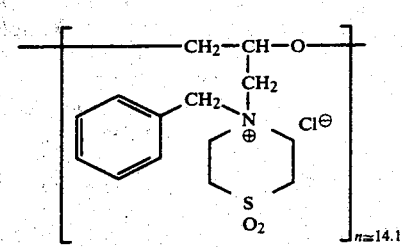

EXAMPLE 5

Polyepichlorohydrin of M.W. 2600 (92 g; 1 eqv.) was heated at 145°-160° C. in a closed pressure reactor with

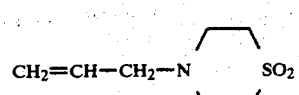

(175 g; 1 eqv.) and 267 g of a 1:1 water, isopropanol mixture. At the end of 12 hours of heating the ionic chloride content was found to be 6.6% indicating 100% reaction. The structure of the product was

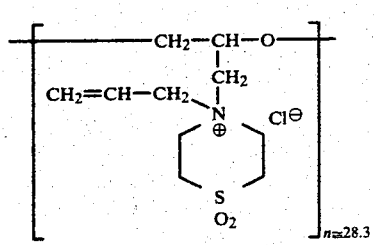

EXAMPLE 6

Polyepichlorohydrin M.W. 1300 (92 g; 1 eqv.) was mixed with

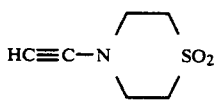

(159 g; 1 eqv.) in a 1:1 mixture of water, isopropanol (251.0 g) and heated in a closed reactor at 145°–155° C. for 12 hours. An analysis for ionic chloride content was 6.7% (Theoretical was 7.0%). The product had the structure

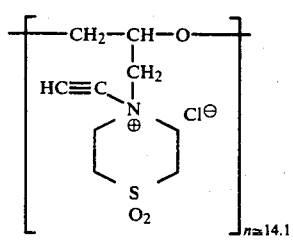

EXAMPLE 7

Polyepichlorohydrin M.W. 2500 (92 g; 1 eqv.) was mixed with

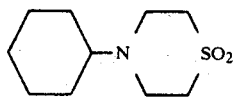

(217 g; 1 eqv.) in a 1:1 mixture of water, isopropanol (309.0 g.) and heated in a closed reactor at 145°–160° C. for 24 hours. The product had the structure

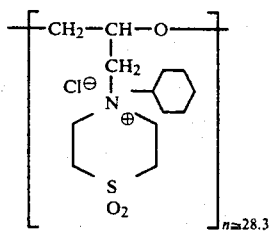

EXAMPLE 8

Polyepichlorohydrin M.W. of 1300 (46 g; 0.5 eqv.) was heated at 150°–160° C. with

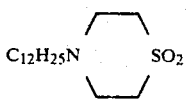

(151 g; 0.5 eqv.) in a 1:1 mixture of water, isopropanol (197.0 g) for 24 hours in a closed reactor. The product had the structure

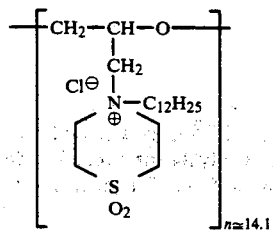

EXAMPLE 9

Polyepichlorohydrin M.W. of 1300 (46 g; 0.5 eqv.) was heated in a closed reactor at 150°–160° with

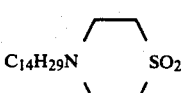

(165 g; 0.5 eqv.) in a 1:1 mixture of water, isopropanol (211.0 g) for 24 hours. The product had the structure

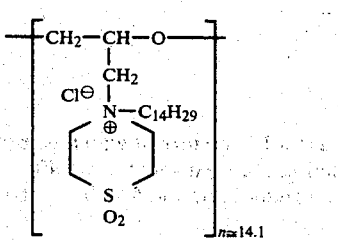

EXAMPLE 10

Polyepichlorohydrin M.W. of 1300 (46 g; 0.5 eqv.) was heated at 145°–160° C. in a closed reactor with

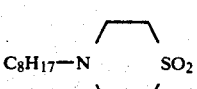

(124 g; 0.5 eqv.) in a 1:1 mixture of water, isopropanol (170 g.) for 24 hours. The product had the structure

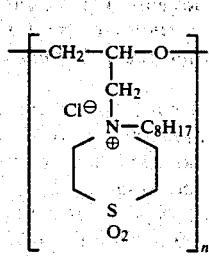

EXAMPLE 11

Polyepiiodohydrin M.W. of 1400 (46 g; 0.5 eqv.) was heated with

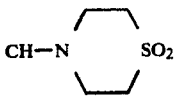

(81.5 g; 0.5 eqv.) in water 127.5 g. in a closed reactor at 140°–150° C. for 8 hrs. Analysis for ionic iodide gave 36.2% (Theoretical was 36.6%) The product had the structure

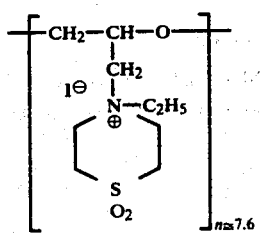

EXAMPLE 12

A mixture of Polyepiiodohydrin M.W. of 1400 (92 g; 0.5 eqv.),

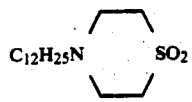

(151 g.; 0.5 eqv.) and a 1:1 mixture of water, isopropanol (243 g) was heated in a closed reactor at 140°–150° C. for 12 hours. The product had the following structure

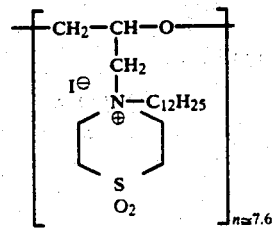

USE AS FLOCCULATING AGENTS

Water Clarification

The present invention relates to a method for the clarification of water containing suspended matter.

According to the present invention clarification of water containing suspended particles of matter is effected by adding to such water the polymers of this invention.

Water containing suspended particles which may be treated by the present invention may have its origin either in natural or artificial sources, including industrial and sanitary sources. Waters containing suspended particles of natural origin are usually surface waters, wherein the particles are suspended soil particles (silt), although subsurface waters may also be treated according to the present invention. Water having its origin in industrial process (including sanitary water) operations may contain many different varieties of suspended particles. These particles are generally the result of the particular industrial or sanitary operation concerned. Prior to discharging such industrial waste waters into natural water courses it generally is desired that the suspended matter be removed.

The present process may likewise be applied to water contained in stock or fish ponds, lakes or other natural or artificial bodies of water containing suspended solids. It may be applied to industrial water supplied either in preparation therefor, during or after use and prior to disposal. It may be applied to sanitary water supplies either for the elimination of suspended solids prior to use for such purposes, or it may be applied to such waters which have become contaminated with impurities from any source.

Most naturally occurring waters contain an amount of simple electrolytes (sodium, potassium, ammonium, calcium, aluminum salts, etc.) in excess of that necessary for the initial aggregation of the ultimate silt particles.

This is likewise true of particles of suspended material in industrial or sanitary waters. The ultimate particles of silt or other materials are therefore naturally somewhat aggregated by reason of the presence of such electrolytes. However, the forces binding such ultimate particles together are not great and moreover are not such as to generally effect either rapid settling rates of the flocculated material or strong enough to prevent deflocculation.

The compositions of the invention cause rapid flocculation and also reinforced the formed aggregates of particles causing a general tightening or bonding together of the initial particles and an increased rate of coagulation and settling, thus forming a less turbid supernatant liquid.

The addition of the compositions of the invention to the water suspension should be made in such a fashion that the resulting flocculation and aggregation of the particles takes place uniformly throughout the body of water. In order to obtain a uniform addition of the compositions of the invention to the water-borne suspension it is generally desirable to prepare a relatively dilute stock solution of the inventive compositions and then to add such solution to the body of water in the proportions indicated above. Clarification may take place either in the natural body of water or it may be caused to take place in hydraulic thickeners of known design.

The amount of inventive compositions to be employed will vary depending upon the amount of the degree of subdivision of the solids to be agglomerated or flocculated, the chemical nature of such solid and the particular inventive compositions employed. In general, I employ at least a sufficient amount of the inventive compositions to promote flocculation. In general, I employ about 0.5–10,000 ppm or more, such as about 1–5,000 ppm, for example about 2–500 ppm, but preferably about 5–25 ppm. Since the economics of these processes are important, no more than the minimum amount required for efficient removal is generally employed. It is desired, of course, to employ sufficient of the inventive compositions so flocculation will take place without causing the formation of stable dispersions.

The precipitating action of the inventive compositions can be employed in the application of loading or filling materials to textiles or paper in order to obtain special effects. As an example, rosin size is often added to paper pulp prior to the formation of the sheet and precipitated in the aqueous pulp by aluminum sulfate (papermaker's alum). While admirably serving this purpose it is recognized that aluminum sulfate is objectionable not only because of its actual corrosiveness upon metals but also because of its hardening effect on organic substances such as cellulose. (II) Water By adding the inventive compositions to the paper machine beater, either prior to or after the addition of size of filler, complete precipitation can be achieved without the use of alum. The resulting paper is obtained thus substantially free of electrolytes and the white water is clear and free of suspended particles. In this connection a difficulty often encountered with alum when applying certain colors to paper, which difficulty is manifested by weakening of the color, is also avoided.

In the processing of fine mineral particles in aqueous suspension the inventive composition flocculating agents will be especially useful. In the processing of ores to separate valuable mineral constituents from undesirable matrix constituents, it is frequent practice to grind the ore into a finely-divided state to facilitate separation steps such as selective flotation and the like. In many ore dressing procedures, the finely-divided ore is suspended in water to form a pulp or slime. After processing, it is usually desirable to dewater the pulps or slimes either by sedimentation or filtering. In such operations, certain ores are particularly troublesome in that the finely-divided ore, when suspended in water, forms a stable slime which settles very slowly, if at all. Such slimes are unsuitable for concentration or dewatering by sedimentation and are difficult to dewater by filtration because of the tendency to clog the pores of the filter, thus leading to excessively, time-consuming and inefficient operation of the filters. In some cases, for example, in certain phosphate mining operations, the formation of very stable suspensions of finely-divided mineral results not only in the loss of considerable valuable mineral as waste but also requires large expenditures for the maintenance of holding ponds for the waste. Similar problems are involved in processing gold, copper, nickel, lead, zinc, iron, such as taconite ores, uranium and other ores, and the inventive flocculating agents will be useful in these operations.

Some specific additional applications for the flocculating agent for the invention, not intended to be limited but merely illustrative are listed below. The inventive composition can be used for the clarification of beers or wines during manufacture. Another use is in processing effluents in pharmaceutical operations for the recovery of valuable products or removal of undesirable by-products. A particularly important use for these flocculating agents is in the clarification of both beet sugar and can sugar juices in their processing. Still another use is for flocculation and recovery of pigments from aqueous suspensions thereof. The inventive composition will be particularly useful in sewage treatment operations as a flocculation agent. A further use is to promote by flocculation the removal of coal from aqueous suspensions thereof. In other words the inventive composition flocculating agents of the invention are generally useful for processing aqueous effluents of all types to facilitate the removal of suspended solids.

A water soluble or water disposable composition, to the extent of effective concentration, is employed.

These compositions can also be employed in the process of flocculating white water and/or recycling of the precipitate solids in the paper making process described in U.S. application Ser. No. 347,023 filed Feb. 24, 1964, now abandoned and other processes described therein.

The following examples are presented by way of illustration and not limitation.

FLOCCULATION EXAMPLE A

Into 500 ml. of a 5% brine solution containing 25 ppm of FeS was introduced a solution containing 5 ppm of the polyquaternary polymer (Example 1). The solution was stirred for 1 minute at 100 r.p.m. on a Phipp and Bird "Floc Stirrer" apparatus. The speed was then reduced to 20-35 r.p.m. for 10 minutes, and then stopped. The floc size and precipitation rate of the floc were excellent. The water color after precipitation was also excellent.

FLOCCULATION EXAMPLE B

To an aqueous suspension of 300 ppm bentonite (Volclay, 625 mesh, American Colloid) was added a solution of the polyquaternary described in Example 3. The polymer dosage was 10 ppm. The solution was stirred for 1 minute at 100 r.p.m. on a "Phipp and Bird" floc stirrer apparatus. The speed was then reduced to 20-35 r.p.m. for 10 minutes, and then stopped. The supernatant liquid was drawn off and analyzed for residual turbidity. The turbidity was 20% of that of the untreated water which also contained 300 ppm of bentonite.

Polymers of the present invention can be employed as flocculating agents in the following industries:
(1) Petroleum industry
(2) Food industry such as in the dairy industry, the canning, freezing and dehydration industries
(3) Metal plating industry
(4) Chemical and pharmaceutical industries
(5) Mining industry, for example, in the phosphate mining industry such as in phosphates slimes
(6) Fermentation industries, such as in alcohol, beer, yeast, antibiotics, etc. production
(7) Tanning industry
(8) Meat packing and slaughter house industry
(9) Textile industry
(10) Sugar refining industry
(11) Coal industry
(12) Soap industry
(13) Sewage purification
(14) Corn starch industry
(15) Fat processing and soap industry
(16) Paper industry.

USE AS A DEMULSIFIER

Most naturally occurring emulsions of petroleum oil and water take the form of a water-in-oil emulsion in which the oil is the continuous phase and tiny droplets of water are dispersed in the oil. Oftentimes, however, reversed emulsions are encountered either in the production, handling or refining of petroleum oil. Reversed emulsions are of a character quite different from the usual water-in-oil emulsions and must be treated in a different manner with different chemicals in order to resolve the reversed emulsion into oil and water phases.

In general, I employ 0.5-10,000 ppm or more, such as 1-5,000 ppm, for example about 2-500 ppm, but preferably 5-50 ppm.

The invention is illustrated by the following example.

DEMULSIFICATION EXAMPLE A

An oil-in-water emulsion was prepared by mixing 25 g. of a non-detergent motor oil with 200 g. of water in a Waring Blender set at high speed. Mixing time was 15 minutes. The resulting product was placed in a separatory funnel and allowed to stand overnight. About three fourths of the lower phase, a very hazy appearing emulsion of oil-in-water was removed from the funnel and recovered. Four batches of the emulsion were prepared and combined. Each of five 100 ml. graduated cylinders was filled to the 100 ml. mark with the emulsion. The first cylinder was set aside as a control while the emulsion in each of the other graduated cylinders was treated with a predetermined quantity of demulsifier. All runs were made at 25° C.

The following table shows the test conditions and results of these tests.

TABLE 1

| Cylinder Number | Demulsifier (ppm) | Appearance after 24 hrs. |
|---|---|---|
| 1 | none (control) | Very hazy |
| 2 | Ex. 1 (25) | Clear |
| 3 | Ex. 2 (25) | Clear |
| 4 | Ex. 3 (25) | Clear |
| 5 | Ex. 4 (25) | Clear |
| 6 | Ex. 5 (25) | Clear |

USE AS A MICROBIOCIDE (I) In Water Treatment

This phase of the present invention relates to the treatment of water. More particularly, it is directed to providing improved means for controlling microbiological organisms including bacteria, fungi, algae, protozoa, and the like. present in water.

It is well known that ordinary water contains various bacteria, fungi, algai, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bacterial, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algai, and all forms of microbial life therein.

(II) A Water Flooding in Secondary Recovery of Oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil-bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon Treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans*, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 25 hours. The absence or presence of growth of the microorganisms was determined by visual inspection by an experienced observer.

Following is a summary of the results of the testing of examples of this invention.

| Compound Example | Concentration of test compound, ppm | Results |
|---|---|---|
| 8 | 40 | Gave control.[1] |
| 9 | 40 | " |
| 10 | 50 | " |
| 12 | 40 | " |

[1]By control is meant that the test compound was biostatic or biocidal - i.e., no growth of the test organism occurred under the test conditions.

CORROSION INHIBITION

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oilwell acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quaternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidazole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consisting of formate esters of the structure:

HCOOR where R is a monoaryl group, an alkyl group having 1 to 6 carbon atoms, cyclo-alkyl residues having 5 to 6 carbon atoms, alkenyl and alknyl groups having 2 to 6 carbon atoms which may contain functional groupins selected from —C—OH, —OH, =C=O, —COH, —SH, and $NH_2$. Examples of the formic acid compound are: methyl formate, ethylformate, benzyl formate, other alkyl and aryl formates, and the like. Other examples include formamide, dimethyl formamide, formanilide, and the like. Mixtures of the esters and mixtures of the amides may be used.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

CORROSION TEST PROCEDURE

In these tests the acid solutions were mixed by diluting concentrated hydrochloric acid with water to the desired concentrations.

Corrosion coupons of 1010 steel (AISI) were pickled in an uninhibited 10% HCl solution for 10 minutes, neutralized in a 10% solution of NaHCO₃, dipped in acetone to remove water and allowed to dry. They were then weighed to the nearest milligram and stored in a desicator.

In most of the tests, a 25 cc/in² acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to lbs./ft²/24 hrs. The factor was calculated as follows:

$$\frac{\frac{144 \text{ in}^2}{\text{ft}^2}}{\frac{454 \text{ g}}{\text{lb}} \times \text{Surface Area of Coupon (in}^2) \times \frac{1 \text{ day}}{24 \text{ hrs}}} = \text{Factor}$$

All tests were carried out under the following conditions.

| | |
|---|---|
| (1) Concentration 3000 ppm | (4) 15% HCl |
| (2) Test Temp. 150° F. | (5) Employing 1010 steel corrosion coupon |
| (3) Time 4 hours | |

The results of these tests are included below:

| Inhibitor | Corrosion rate (lbs./ft²/day) |
|---|---|
| Ex. 3 | 0.085 |
| Ex. 4 | 0.054 |
| Ex. 6 | 0.042 |
| Ex. 7 | 0.050 |
| Ex. 8 | 0.038 |
| Ex. 9 | 0.037 |
| Ex. 12 | 0.030 |
| Blank | 2.02 |

Applications in which the inhibitors of the present invention are particularly useful include oil-well acidizing solutions, metal pickling, cleaning and polishing baths, boiler cleaning compositions and the like.

I claim:

1. A process of clarifying aqueous systems containing suspended particles of matter which comprises adding to such systems a thiazine quaternary ammonium salt of polyepihalohydrin wherein the nitrogen atom of the thiazine moiety is attached to the polymeric chain through a —CH₂— group in an amount sufficient to clarify said aqueous system, and flocculating said suspended particles of matter to clarify said aqueous system.

2. The process of claim 1 where the thiazine quaternary ammonium salt of polyepihalohydrin contains the polymer unit

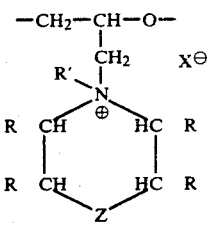

where Z is S, SO, or SO₂, R is hydrogen or a hydrocarbon group, R' is a hydrocarbon group, and X is halogen.

3. The process of claim 1 where the thiazine quaternary ammonium salt of polyepihalohydrin contains the polymer unit

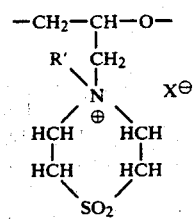

where R' is a hydrocarbon group and X is halogen.

4. The process of claim 1 where the thiazine quaternary ammonium salt of polyepihalohydrin contains the polymer unit

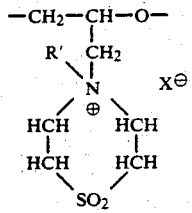

where R' is alkyl, alkenyl, alkinyl, aryl or aralkyl.

5. The process of claim 1 where the thiazine quaternary ammonium salt of polyepihalohydrin contains the polymer unit

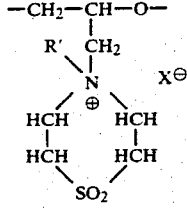

where R' is alkyl, alkenyl, alkinyl, aryl or aralkyl and X is chlorine or iodine.

6. The process of claim 1 where the thiazine quaternary ammonium salt of polyepihalohydrin is

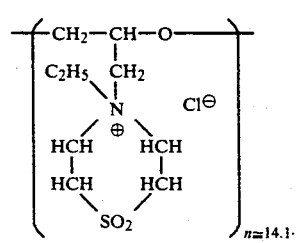
7. The process of claim 1 where the thiazine quaternary ammonium salt of polyepihalohydrin is
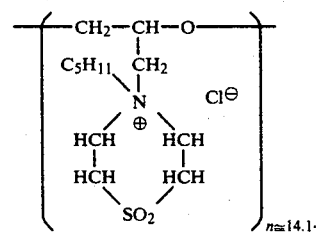
* * * * *